United States Patent
Naka et al.

(10) Patent No.: US 11,370,572 B2
(45) Date of Patent: Jun. 28, 2022

(54) SURFACE TREATMENT METHOD AND SURFACE TREATMENT DEVICE FOR RESIN VESSEL

(71) Applicant: SHIBUYA CORPORATION, Kanazawa (JP)

(72) Inventors: Toshiaki Naka, Kanazawa (JP); Kei Matsui, Kanazawa (JP); Tokuo Nishi, Kanazawa (JP); Masanari Ejiri, Kanazawa (JP); Noriaki Ikenaga, Nonoichi (JP)

(73) Assignee: SHIBUYA CORPORATION, Kanazawa (JP)

( * ) Notice: Subject to any disclaimer, the term of this patent is extended or adjusted under 35 U.S.C. 154(b) by 152 days.

(21) Appl. No.: 16/006,278

(22) Filed: Jun. 12, 2018

(65) Prior Publication Data

US 2018/0362202 A1 Dec. 20, 2018

(30) Foreign Application Priority Data

Jun. 15, 2017 (JP) .............................. JP2017-118009

(51) Int. Cl.
*B65B 55/24* (2006.01)
*C08J 7/12* (2006.01)
(Continued)

(52) U.S. Cl.
CPC .............. *B65B 55/24* (2013.01); *A61L 2/087* (2013.01); *B29C 71/04* (2013.01); *C08J 7/123* (2013.01);
(Continued)

(58) Field of Classification Search
None
See application file for complete search history.

(56) References Cited

U.S. PATENT DOCUMENTS 3,296,999 A * 1/1967 Gamble .............. B05B 13/0442
118/680
3,690,289 A * 9/1972 Frank .................. B05B 13/0278
118/720
(Continued)

FOREIGN PATENT DOCUMENTS

EP 1849746 A1 10/2007
FR 2872148 A1 12/2005
(Continued)

OTHER PUBLICATIONS

European Search Report for corresponding application No. 18177604.8, dated Nov. 20, 2018 (9 pages).
(Continued)

*Primary Examiner* — Charles Capozzi
(74) *Attorney, Agent, or Firm* — Flynn Thiel, P.C.

(57) ABSTRACT

A surface treatment method and a surface treatment device 2 for a resin vessel 1 forms a coating or performs surface modification on the surface of the resin vessel 1. In a sterilized environment as well as an environment with a pressure equal to or higher than the atmospheric pressure, a material for the coating or the surface modification is attached to at least one of an inner surface and an outer surface of the resin vessel 1, and the resin vessel 1, to which the material is attached, is irradiated with an electron beam to perform the coating or the surface modification. It is possible to form the coating or perform the surface modification on the resin vessel at a high speed.

6 Claims, 5 Drawing Sheets

(51) Int. Cl.
*B29C 71/04* (2006.01)
*A61L 2/08* (2006.01)
*B05D 7/22* (2006.01)
*B05D 3/06* (2006.01)
*B29C 35/08* (2006.01)
*B05D 7/02* (2006.01)

(52) U.S. Cl.
CPC ............ *B05D 3/06* (2013.01); *B05D 7/02* (2013.01); *B05D 7/227* (2013.01); *B29C 2035/0877* (2013.01); *C08J 2300/22* (2013.01); *C08J 2367/02* (2013.01)

(56) References Cited

U.S. PATENT DOCUMENTS

| | | | | |
|---|---|---|---|---|
| 4,850,300 | A * | 7/1989 | Kraft | B05B 13/0421 118/63 |
| 6,231,939 | B1 | 5/2001 | Shaw et al. | |
| 2003/0219547 | A1 * | 11/2003 | Arnold | B08B 7/00 427/569 |
| 2005/0097863 | A1 * | 5/2005 | Taggart | B65B 55/10 53/167 |
| 2005/0191435 | A1 | 9/2005 | Bauman | |
| 2007/0154621 | A1 * | 7/2007 | Raad | A61L 31/16 427/2.1 |
| 2007/0253861 | A1 * | 11/2007 | Naka | A61L 2/087 422/22 |
| 2009/0208369 | A1 * | 8/2009 | Olsson | A61L 2/186 422/28 |
| 2010/0132307 | A1 * | 6/2010 | Nishino | B67C 7/0073 53/167 |
| 2010/0199604 | A1 * | 8/2010 | Fischer | B67C 7/0073 53/425 |
| 2010/0202918 | A1 * | 8/2010 | Kobayashi | B67C 7/0073 422/22 |

FOREIGN PATENT DOCUMENTS

| | | |
|---|---|---|
| JP | 3952695 B2 | 2/2002 |
| JP | 2007-070734 A | 3/2007 |
| JP | 5460756 B2 | 6/2012 |

OTHER PUBLICATIONS

"Study of barrier properties and chemical resistance of recycled PET coated with amorphous carbon through a plasma enhanced chemical vapour deposition (PECVD) process", by S.A. Cruz et al, Food Additives and Contamina, vol. 23, Jan. 2006, English abstract only (1 page).

* cited by examiner

SURFACE TREATMENT METHOD AND SURFACE TREATMENT DEVICE FOR RESIN VESSEL

BACKGROUND OF THE INVENTION

Field of the Invention

The present invention relates to a surface treatment method and a surface treatment device for a resin vessel, which perform coating or modification treatment on the surface of the resin vessel.

Description of the Related Art

Nowadays, in order to prevent the oxidation and aroma loss of beverages or the like in a resin vessel such as a pet bottle, the surface of the resin vessel has been coated or modified to reduce the gas permeability of the resin vessel.

For example, Japanese Laid-Open Patent Application No. 2007-70734 describes a method in which a resin vessel is located in a depressurized environment, a material gas for coating is supplied to the inside of the resin vessel, and further, a plasma is generated between an outer electrode provided outside the resin vessel and an inner electrode provided inside the resin vessel, to activate the material gas and perform coating on the inner surface of the resin vessel.

Japanese Patent No. 3952695 describes a method in which a resin vessel is accommodated into a storage chamber, the storage chamber is supplied with a material gas while being depressurized, a plasma is further generated in the storage chamber, a positive high voltage pulse is applied to an electrode inserted into the resin vessel, and ions are implanted into a surface layer of the resin vessel to modify the surface.

However, in Japanese Laid-Open Patent Application No. 2007-70734 and Japanese Patent No. 3952695, the resin vessel needs to be placed in the depressurized environment so as to generate the plasma and, in that case, the time for forming the depressurized environment is required, which has caused limitations on treatment capacity.

In view of such a problem, the present invention provides a surface treatment method and a surface treatment device for a resin vessel which are capable of performing coating or modification treatment on the surface of a resin vessel at a high speed.

SUMMARY OF THE INVENTION

That is, a surface treatment method for a resin vessel according to the first embodiment of the invention is a surface treatment method for a resin vessel, which performs coating or surface modification on a surface of the resin vessel, characterized in that the method includes: attaching a material for coating or surface modification to at least one of an inner surface and an outer surface of the resin vessel in an environment with a pressure equal to or higher than atmospheric pressure; and irradiating the resin vessel, to which the material is attached, with an electron beam.

Further, a surface treatment device for a resin vessel according to the second embodiment of the invention is a surface treatment device for a resin vessel, which performs coating or surface modification on a surface of the resin vessel, characterized in that the device includes: a chamber with pressure set to be equal to or higher than atmospheric pressure; a vessel carrier unit configured to carry the resin vessel in the chamber; a material injection unit configured to attach a material for coating or surface modification to at least one of an inner surface and an outer surface of the resin vessel; and an electron beam irradiation unit configured to irradiate the resin vessel, to which the material is attached, with an electron beam.

With the surface treatment method for the resin vessel according to the first embodiment of the invention and the surface treatment device for the resin vessel according to the second embodiment of the invention described above, the resin vessel, to which the material for coating or surface modification is attached, is irradiated with the electron beam, whereby it is possible to form a coating or perform modification treatment on the surface of the resin vessel.

At this time, the environment is set at a pressure equal to or higher than the atmospheric pressure, thereby eliminating the need for the depressurization step as in Japanese Laid-Open Patent Application No. 2007-70734 and Japanese Patent No. 3952695 described above and enabling a high-speed treatment.

Further, the resin vessel can be sterilized simultaneously due to the irradiation with the electron beam, thereby eliminating the need to separately perform the coating or the surface treatment on the resin vessel and the sterilization and thereby enabling an efficient treatment.

DETAILED DESCRIPTION OF THE PREFERRED EMBODIMENTS

Figure 1:
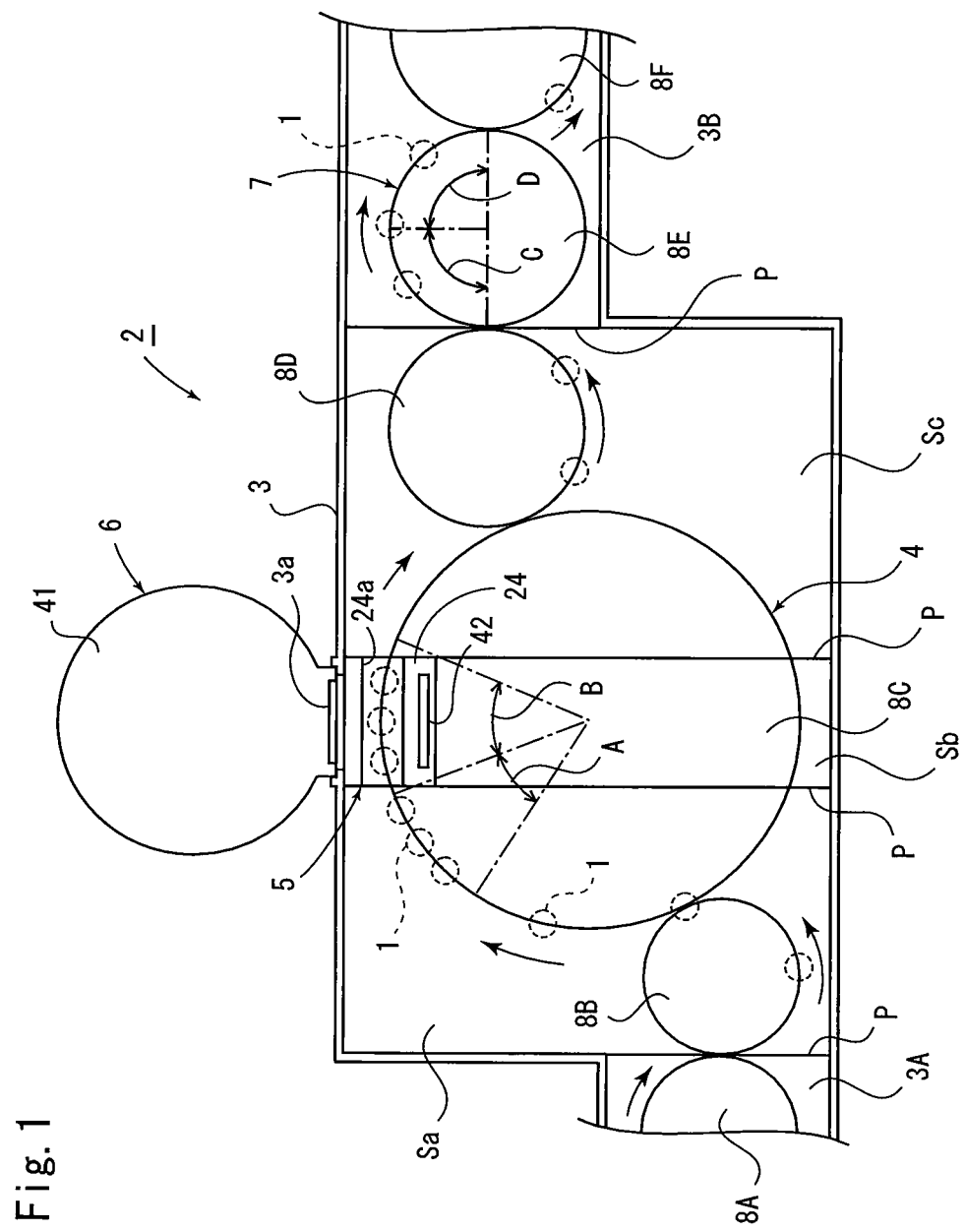
FIG. 1 is a configuration view of a coating device according to the present invention.

The illustrated examples will be described below. FIG. 1 shows a surface treatment device 2 according to a first embodiment, which performs coating or modification treatment on the surface of a resin vessel 1 such as a pet bottle and constitutes a part of a filling line for filling the resin vessel 1 with a beverage.

Figure 2:
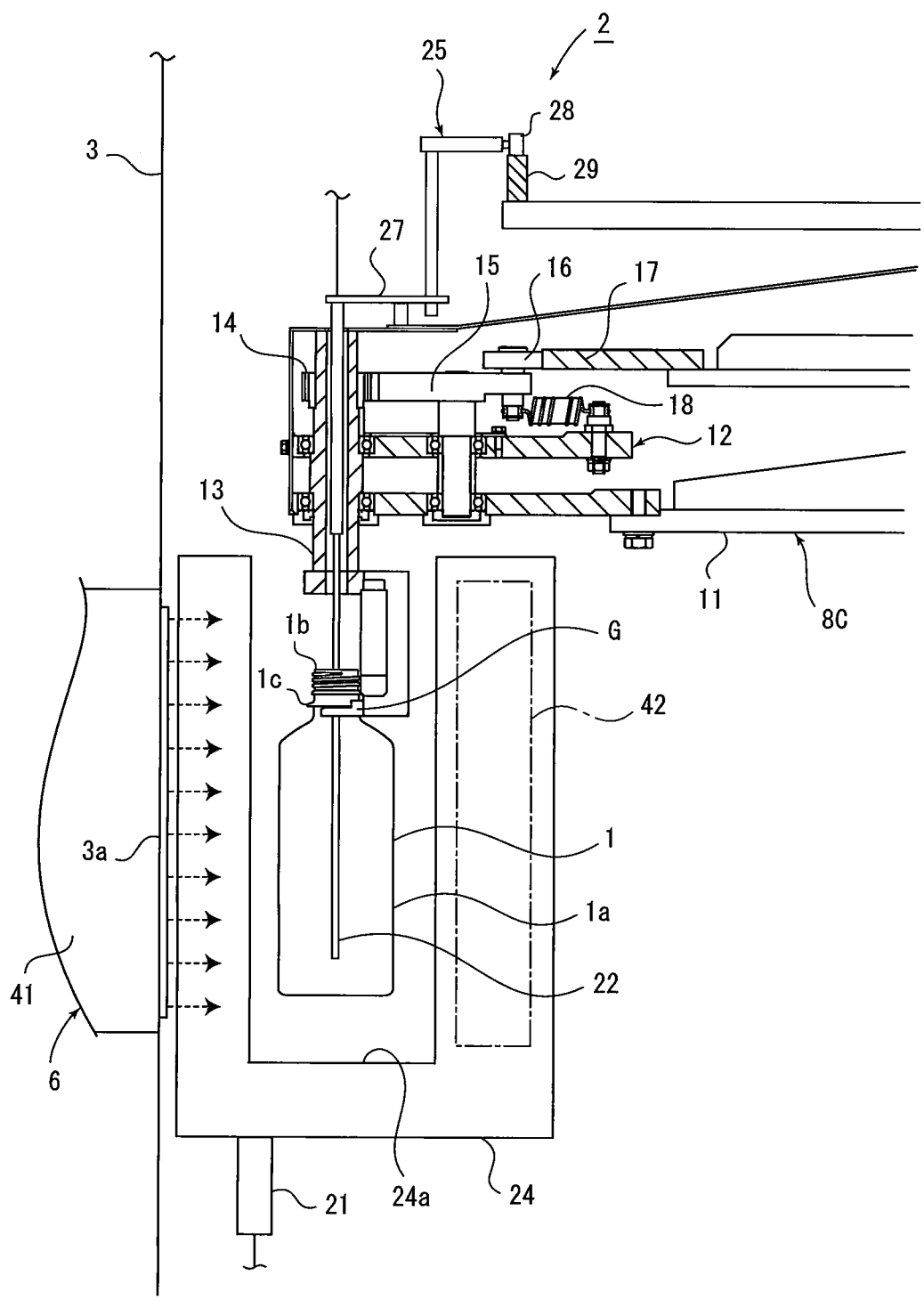
FIG. 2 is a sectional view of the coating device in FIG. 1.

As shown in FIG. 2, the resin vessel 1 includes a body 1a filled with a beverage or the like, a neck portion 1b provided in an upper part of the body 1a and mounted with a cap, and a flange portion 1c provided in a lower part of the neck portion 1b, and a lower part of the flange portion 1c is supported at the time of carrying the resin vessel 1.

By performing coating or surface modification on the resin vessel 1, it is possible to reduce the gas permeability of the resin vessel 1 and prevent oxidation and aroma loss of a beverage such as beer and wine.

In the present example, a coating is formed or surface modification is performed on the inner surface and the outer surface of the resin vessel 1. First, a material for the coating or the surface modification is attached to the outer surface and the inner surface of the resin vessel 1, and then the resin vessel 1, to which the material is attached, is irradiated with an electron beam, to perform the coating or the surface modification.

Various materials can be used as the material for the coating or the surface modification. For example, a material of a component containing a carbohydrate such as acetylene, toluene, or xylene, a material of a component containing silane such as tetramethylsilane, or some other material can be used.

The surface treatment device 2 includes: a sterilization chamber 3 with its inside kept in a sterilized state; a vessel carrier unit 4 that carries the resin vessel 1 in the sterilization chamber 3; a material injection unit 5 that attaches the material to the resin vessel 1; an electron beam irradiation unit 6 that irradiates the resin vessel 1, to which the material is attached, with an electron beam; and an aeration unit 7 that discharges the material for the surface treatment and the like from the inside of the resin vessel 1.

A wall surface constituting the sterilization chamber 3 is made of lead that shields the electron beam, with which the resin vessel 1 is irradiated, and the inside of the sterilization chamber 3 is kept in the sterilized state by a sterilized air supply unit, not shown.

Further, a take-in room 3A and a taken-out room 3B are respectively connected to the upstream side and the downstream side of a path for carrying by the vessel carrier unit 4 in the sterilization chamber 3, while being kept in an airtight and sterilized state, and a partition plate P is provided on a boundary between these chambers.

The pressure inside the sterilization chamber 3 is set to be higher than the atmospheric pressure and to be higher than the pressure in each of the take-in room 3A and the taken-out room 3B, so that a foreign material from the outside is prevented from entering the sterilization chamber 3.

The inside of the sterilization chamber 3 is further divided into three spaces Sa to Sc with two partition plates P. The partition plate P provided between the spaces Sa and Sb divides the space into an inner surface injection section A in which the material is attached to the inner surface of the resin vessel 1 described below and an electron beam irradiation section B in which irradiation is performed with the electron beam and the material is attached to the outer surface of the resin vessel 1. The partition plate P provided between the spaces Sb and Sc divides the space into the electron beam irradiation section B and a space on the downstream side thereof.

The spaces Sa to Sc are set such that the pressure in the space located on the downstream side is higher than the pressure in the space located on the upstream side. The material injected in the inner surface injection section A is prevented from entering into the space Sb between the space Sa and the space Sb, and the material injected in the electron beam irradiation section B is prevented from entering into the space Sc between the space Sb and the space Sc.

When the material is not injected in the electron beam irradiation section B, it is sufficient that the partition plate P between the spaces Sb and Sc is omitted and the pressure in the space Sb+Sc is made higher than the pressure in the space Sa.

The vessel carrier unit 4 includes first to sixth star wheels 8A to 8F provided from the take-in room 3A to the taken-out room 3B of the sterilization chamber 3 and can continuously carry the resin vessel 1 at a high speed.

In the present example, the injection of the material and the irradiation with the electron beam, intended to coat the resin vessel 1, are performed on the path along which the resin vessel 1 is carried by the third star wheel 8C.

Grippers G for holding the resin vessel 1 are provided on each of the first to sixth star wheels 8A to 8E, and at each reception and passing position where the star wheels are adjacent to each other, the resin vessel 1 is passed from the gripper G on the upstream star wheel to the gripper G on the downstream star wheel.

FIG. 2 shows a sectional view showing positions of the resin vessel 1 carried by the third star wheel 8C and the electron beam irradiation unit 6. The third star wheel 8C includes a rotation table 11 rotated by a drive unit, not shown, and the grippers G are provided at regular intervals along the outer periphery of the rotation table 11.

Each gripper G includes a pair of holding members energized by a spring, and a lower part of the flange portion 1c of the resin vessel 1 is sandwiched between the holding members. Note that the gripper G having such a configuration is conventionally known, and hence the detailed description thereof will be omitted.

The gripper G of the present example is provided on the rotation table 11 so as to be horizontally rotatable by the rotation unit 12, thereby rotating the resin vessel 1 held by the gripper G.

The rotation unit 12 includes: a rotation element 13, which defines a rotation axis, rotatably provided on the rotation table 11; a pinion gear 14 provided at the upper end of the rotation element 13; a segment gear 15 swingably provided on the rotation table 11 and meshed with the pinion gear 14; a cam follower 16 coupled to the segment gear 15; and a cam 17 provided separately from the rotation table 11 and configured to move the cam follower 16.

The segment gear 15 rotates the rotation element 13 by being meshed with the pinion gear 14, a spring 18 with one end coupled to the rotation table 11 is coupled to the segment gear 15, and the cam follower 16 is located on the center side of the rotation table 11 by the energizing force of the spring 18.

When the cam follower 16 follows the cam 17 and moves to the outer peripheral side of the rotation table 11, the segment gear 15 swings accordingly, and the rotation element 13 integrally rotates with the gripper G via the pinion gear 14.

In the present example, the gripper G is rotated by 180° so that one side surface and the other side surface of the resin vessel 1 held by the gripper G are each turned to the outer peripheral side of the rotation table 11.

The material injection unit 5 is comprised of an outer surface nozzle 21 that attaches the material to the outer surface of the resin vessel 1, an inner surface nozzle 22 that attaches the material to the inner surface, and a supply unit 23 that supplies the material to the outer surface nozzle 21 and the inner surface nozzle 22.

The outer surface nozzle 21 is provided on the bottom surface of a hollow injection booth 24 set up inside the sterilization chamber 3, and the injection booth 24 is provided in the electron beam irradiation section B in which the irradiation is performed by the electron beam irradiation unit 6, as shown in FIG. 1.

Figure 3:
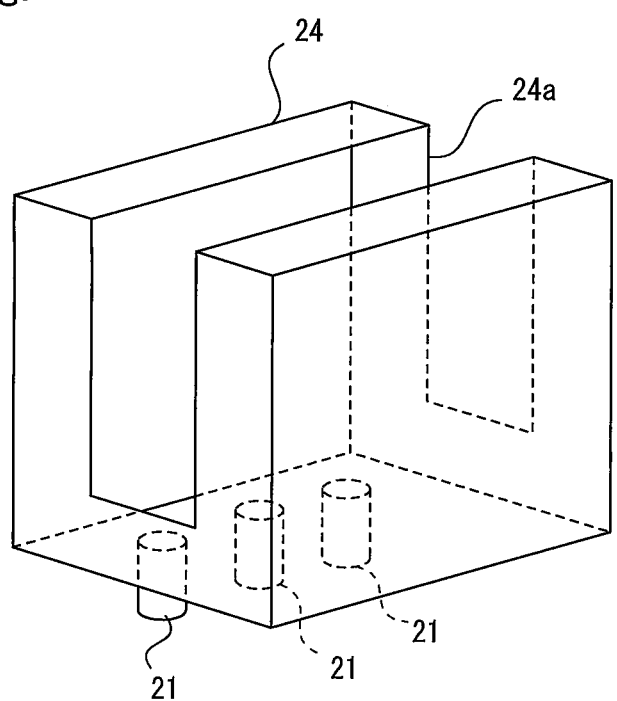
FIG. 3 is a perspective view of an injection booth.

FIG. 3 shows a perspective view of the injection booth 24 having a configuration where a slit 24a, which is passable by the resin vessel 1 carried by the vessel carrier unit 4, is formed in the center of a hollow box-shaped body having a shape that is substantially a rectangular parallelepiped.

The longitudinal length of the injection booth 24 is set equivalent to or slightly larger than the length of the electron beam irradiation section B in which the irradiation is performed by the electron beam irradiation unit 6, and on the bottom part of the injection booth 24, a plurality of the outer surface nozzles 21 are provided along the carrier path for the resin vessel 1.

With such a configuration, when the resin vessel 1 reaches the electron beam irradiation section B by the vessel carrier unit 4, the resin vessel 1 passes the slit 24a formed in the injection booth 24, and during the passing, the resin vessel 1 is exposed to the inner space of the injection booth 24.

The outer surface nozzle 21 then injects the material to the inside of the injection booth 24, so that it is possible to attach the material to the outer surface of the resin vessel 1 and prevent the injected material from scattering outside the injection booth 24.

The outer surface nozzle 21 is disposed on the outer peripheral side of the rotation table 11 with respect to the center of the carried resin vessel 1, and a larger amount of material is injected to the side where the irradiation is performed with the electron beam by the electron beam irradiation unit 6.

The inner surface nozzle 22 is provided at the same intervals as the grippers G provided on the rotation table 11 and provided liftably by a lifting unit 25 while vertically passing through the inside of the tubular rotation element 13 pivotally supported by the rotation table 11. Further, the inner surface nozzle 22 is provided rotatably by a rotary joint 22a provided on the upper part of the inner surface nozzle 22.

Figure 4:
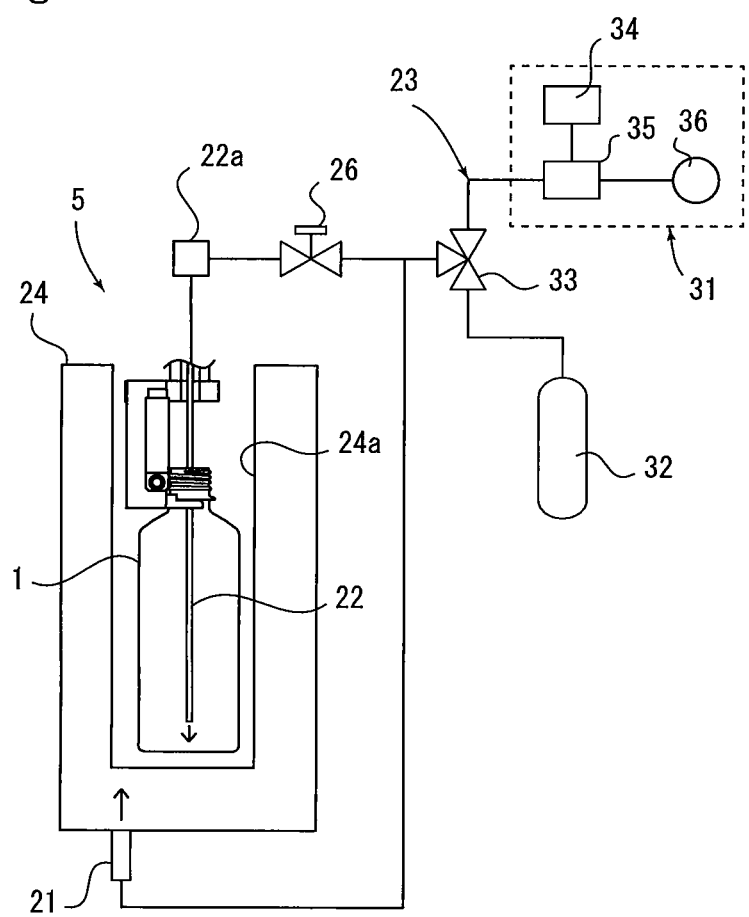
FIG. 4 is a circuit diagram of a material injection unit.

The inner surface nozzle 22 controls the supply and stoppage of the material with an opening/closing valve 26 shown in FIG. 4, and in the present example, the inner surface nozzle 22 injects the material to the inside of the resin vessel 1 in the inner surface injection section A set on the upstream side of the electron beam irradiation section B shown in FIG. 1.

Moreover, the inner surface nozzle 22 of the present example is comprised of a metal member having a tubular shape and constitutes an earth electrode bar for preventing electrification inside the resin vessel 1 at the time of irradiating the resin vessel 1 with the electron beam by the electron beam irradiation unit 6 as described below.

The lifting unit 25 is comprised of a support member 27 that supports the inner surface nozzle 22, a cam follower 28 provided in the support member 27, and a cam 29 provided separately from the rotation table 11. The inner surface nozzle 22 is vertically lifted or lowered by the cam follower 28 following the cam 29 and moving vertically.

Specifically, when the third star wheel 8C receives the resin vessel 1 from the second star wheel 8B, the lifting unit 25 lowers the inner surface nozzle 22 to the inside of the resin vessel 1, and when the third star wheel 8C passes the resin vessel 1 to the fourth star wheel 8D, the lifting unit 25 lifts and removes the inner surface nozzle 22 to the outside of the resin vessel 1.

As shown in FIG. 4, the material injection unit 5 includes: a vaporization supply unit 31 that vaporizes a liquid material and then supplies the vaporized material; a gas material tank 32 that supplies a gaseous material; and a three-way valve 33 for selectively supplying the vaporized material or the gaseous material to the inner surface nozzle 22 and the outer surface nozzle 21.

The vaporization supply unit 31 includes a liquid material tank 34 that accommodates the liquid material, a vaporization unit 35 that vaporizes the liquid material, and a feeding unit 36 that feeds the vaporized material. The vaporization unit 35 vaporizes the liquid material supplied from the liquid material tank 34, and the feeding unit 36 feeds the vaporized material.

Further, the gaseous material is accommodated in the gas material tank 32, and by the inner pressure of the gas material tank 32, the gaseous material is discharged.

Although the material vaporized by the vaporization unit 35 or the gaseous material is attached to the resin vessel 1 in the present example, a liquid may be sprayed to attach the material to the resin vessel 1.

However, it is difficult to attach the liquid material uniformly to the entire surface of the resin vessel 1 carried continuously, so that the vaporized or gaseous material as described above is desirably attached.

The three-way valve 33 supplies either the material vaporized by the vaporization supply unit 31 or the gaseous material provided by the gas material tank 32 to the inner surface nozzle 22 and the outer surface nozzle 21.

That is, in the surface treatment device 2 of the present example, it is possible to form a coating made up of a different material in response to a request. For example, when a toluene-based coating is to be formed, liquid toluene can be vaporized by the vaporization unit 35, and for example when an acetylene-based coating is to be formed, gaseous acetylene can be supplied from the gas material tank 32.

Then a pipe from the supply unit 23 toward the inner surface nozzle 22 and the outer surface nozzle 21 is divided in the middle, and of the divided pipes, the divided pipe on the inner surface nozzle 22 side is provided with the opening/closing valve 26 for stopping the supply of the material to the inner surface nozzle 22.

The electron beam irradiation unit 6 includes an irradiation machine 41 that is provided outside an irradiation window 3a provided on the side surface of the sterilization chamber 3 and performs irradiation with the electron beam.

The irradiation machine 41 is conventionally known and the detailed description thereof will thus be omitted, but the irradiation machine 41 irradiates the resin vessel 1 with the electron beam by heating a filament inside a vacuum chamber to generate thermoelectrons, accelerating the electrons with a high voltage to form a high-speed electron beam, and then causing the electron beam to pass through a film made of a metal such as Ti which is formed on the irradiation window 3a.

When the resin vessel 1, to which the material is attached, is irradiated with the electron beam, as described above, the material is activated and an individual component of the material is attached to the surface of the resin vessel 1 to form a coating.

Here, the irradiation machine 41 of the present example can be set so as to perform irradiation with an electron beam at an acceleration voltage of 300 kV, a current of 5 mA, and a dose of 3.3 kG, but other settings can also be used so long as the resin vessel 1 can be sterilized by irradiation with the electron beam as described below while the material for the coating is activated.

The electron beam, applied from the irradiation machine 41 and transmitted through the resin that forms the resin vessel 1, attempts electrification inside the resin vessel 1, but the inner surface nozzle 22 as the grounded electrode bar releases this electron beam to the outside of the resin vessel 1.

Further, a beam catcher 42 for absorbing the applied electron beam is provided in a position facing the irradiation window 3a. The beam catcher 42 is provided inside the injection booth 24 and on the opposite side of the resin vessel 1 from the irradiation machine 41, so as to absorb the applied electron beam and prevent the diffusion of the electron beam to the outside.

Further, according to the present example, irradiating the material attached to the resin vessel 1 with the electron beam also enables the surface modification of the resin vessel 1 instead of the coating described above.

As described above, when the resin vessel 1, to which the material is attached, is irradiated with the electron beam, the material for the coating is activated to come into an unstable state, but at this time, the material constituting the resin vessel 1 is also activated to come into an unstable state.

Thereafter, the above coating is formed when the activated coating material is attached to the surface of the resin vessel 1, but the surface modification is performed on the resin vessel 1 when the material is actively bound to the activated material surface of the resin vessel 1 to change the composition of the material surface.

Note that one of the coating and the surface modification may be performed, or both of those may be simultaneously performed, depending on the material constituting the resin vessel 1 and the type of the material for each of the coating and the surface modification, the time for irradiation with the electron beam, and the like.

Further, the electron beam irradiation unit 6 of the present example can sterilize the resin vessel 1 as well as forming the coating or performing the surface modification by irradiating the material attached to the resin vessel 1 with the electron beam.

By sterilizing the resin vessel 1 simultaneously with performing the coating or the surface modification on the resin vessel 1 as thus described, the operation is made efficient and the need is eliminated for separately providing the surface treatment device 2 and a sterilizer.

Note that sterilizing the resin vessel 1 with an electron beam is publicly known in an electron beam sterilizer according to Japanese Patent No. 5460756 filed by the present applicant, and hence the detailed description thereof will be omitted.

Figure 5:
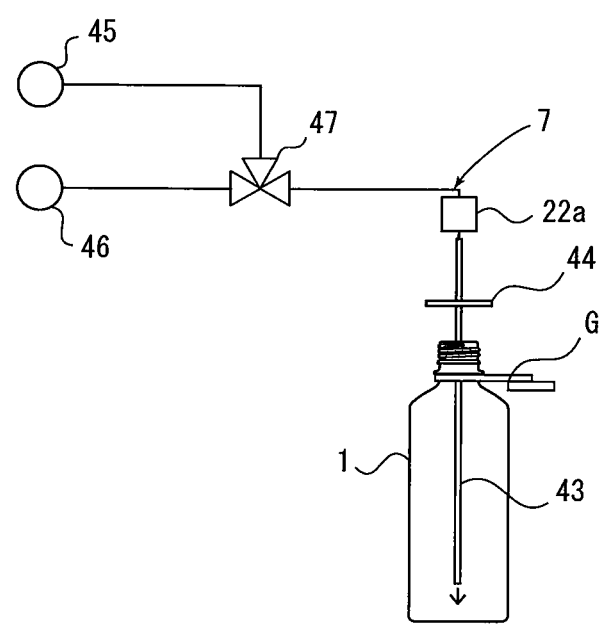
FIG. 5 is a circuit diagram of aeration unit.

The aeration unit 7 is provided in the fifth star wheel 8E in FIG. 1, and FIG. 5 shows a sectional view of the fifth star wheel 8E.

The fifth star wheel 8E is also provided with the grippers G for holding the resin vessel 1 at regular intervals, and this gripper G is also configured to hold the lower part of the flange portion 1c of the resin vessel 1 from both sides by the energizing force of a spring, not shown.

The aeration unit 7 is comprised of: an aeration nozzle 43 that is inserted to the inside of the resin vessel 1; a lifting unit 44 that lifts or lowers the aeration nozzle 43; an air feeding unit 45 that supplies cleaned air to the aeration nozzle 43; and a suction unit 46 that supplies a negative pressure to the aeration nozzle 43 to exhaust the air from the resin vessel 1.

A three-way valve 47 is provided between the air feeding unit 45/suction unit 46 and the aeration nozzle 43, and the air from the air feeding unit 45 and the negative pressure from the suction unit 46 are switched to be supplied to the aeration nozzle 43.

Then, as shown in FIG. 1, in the fifth star wheel 8E, the resin vessel 1 is carried between a position for reception from the fourth star wheel 8D and a position for passing to the sixth star wheel 8F, and in the direction in which the resin vessel 1 is carried, a suction section C in which sucking is performed by the suction unit 46 is on the upstream side while an air supply section D in which the air is supplied from the air feeding unit 45 is on the downstream side.

The lifting unit 44 has a similar configuration to that of the lifting unit 25 for lifting or lowering the inner surface nozzle 22 and the detailed description thereof will thus be omitted. However, from the position for reception from the fourth star wheel 8D toward the position for passing to the sixth star wheel 8F, the aeration nozzle 43 is inserted inside the resin vessel 1, and in the other position, the aeration nozzle 43 is removed to a place above the resin vessel 1.

In the following, a description will be given of a surface treatment method for performing coating or surface modification on the resin vessel 1 by using the surface treatment device 2 having the above configuration. Here, the inside of the sterilization chamber 3 is kept in the sterilized state and set at a pressure higher than the atmospheric pressure.

First, when the resin vessel 1 is carried by the vessel carrier unit 4 and passed from the second star wheel 8B to the third star wheel 8C, the inner surface nozzle 22 is lowered by the lifting unit 25 and inserted to the inside of the resin vessel 1.

Subsequently, when the resin vessel 1 carried by the third star wheel 8C reaches the inner surface injection section A, the step of attaching the material for the surface treatment to the inner surface of the resin vessel 1 by using the inner surface nozzle 22 is performed.

Specifically, in the supply unit 23, the three-way valve 33 is controlled so as to supply the material from either the vaporization unit 35 or the gas material tank 32 to the inner surface nozzle 22, and the opening/closing valve 26 is opened only during the time when the inner surface nozzle 22 moves in the inner surface injection section A.

This leads to attachment of the material injected from the inner surface nozzle 22 to the entire inner surface of the resin vessel 1.

Note that the inner surface injection section A in which the material is injected by the inner surface nozzle 22 may overlap with the electron beam irradiation section B, but when the resin vessel 1 is to be carried at a high speed, it is desirable to set the inner surface injection section A on the upstream side of the electron beam irradiation section B as in the present example.

Next, the step of attaching the material to the outer surface of the resin vessel 1 is performed simultaneously with the step of irradiating the resin vessel 1 with the electron beam.

When the resin vessel 1 carried by the vessel carrier unit 4 reaches the electron beam irradiation section B, the resin vessel 1 moves inside the injection booth 24 along the slit 24a, and during the movement, the material injected by the outer surface nozzle 21 is attached to the outer surface of the resin vessel 1.

The electron beam irradiated by the electron beam irradiation unit 6 then activates the material attached to the outer surface and the inner surface of the resin vessel 1, whereby a coating is formed or surface modification is performed on each of the outer surface and the inner surface of the resin vessel 1.

Further, when the resin vessel 1 enters the electron beam irradiation section B, the rotation unit 12 rotates the gripper G by 180° at the required timing, and thereby one side surface and the other side surface of the resin vessel 1 are irradiated with the electron beam to enable the forming of a coating or performing of surface modification on the entire surface of the resin vessel 1.

Electrons and ions existing inside the resin vessel 1 are drawn by the inner surface nozzle 22 as the grounded electrode bar and then caused to flow to the outside, so that the electrification of the resin vessel 1 can be prevented.

Moreover, in the present example, the resin vessel 1 can be sterilized by irradiating the resin vessel 1 with the electron beam in the electron beam irradiation section B, and it is thus possible to simultaneously perform the surface treatment, such as the coating or the modification, and the sterilization on the surface of the resin vessel 1 without providing a sterilizer other than the surface treatment device 2.

The resin vessel 1, on the inner surface and the outer surface of which the coating or the surface modification have been performed, is then passed from the third star wheel 8C to the fifth star wheel 8E via the fourth star wheel 8D, and the step of replacing the inside air with clear air is performed.

When the resin vessel 1 is passed to the fifth star wheel 8E, the aeration nozzle 43 is inserted to the inside of the resin vessel 1 by the lifting unit 44, and in the upstream suction section C, a negative pressure is supplied to the inside of the resin vessel 1 to cause a suction of the gas inside the resin vessel 1.

At this time, it is possible to suck and discharge the material left inside the resin vessel 1, ozone generated inside the resin vessel 1 due to the irradiation with the electron beam, a coating peeled inside the resin vessel 1, and the like.

When the gas inside the resin vessel 1 is discharged in this manner, in the air supply section D set on the downstream side, the cleaned air is supplied to the inside of the resin vessel 1 and the gas inside the resin vessel 1 is replaced with the cleaned gas.

The resin vessel 1 having completed the aeration is further carried by the vessel carrier unit 4 and filled with a beverage or the like in a post process, not shown.

As described above, according to the surface treatment device 2 and the surface treatment method in the present example, depressurization is not necessary, the resin vessel 1 can be continuously carried using the star wheels, and the surface treatment can be performed on the inner surface and the outer surface of the resin vessel 1 at a high speed.

Further, in the present example, it is possible to sterilize the resin vessel 1 with the electron beam simultaneously with activating the material by irradiation with the electron beam to perform the coating or the surface modification, thereby enabling the efficient performance of these operations and eliminating the need to provide independent devices.

When the coating or the surface modification is to be performed only on the outer surface of the resin vessel 1 in the configuration of the first example, it is sufficient that the material is not injected from the inner surface nozzle 22 in the above configuration.

As another configuration, a solid grounded electrode bar may be used in place of the inner surface nozzle 22, or the inner surface nozzle 22 may inject sterilized air or nitrogen instead of injecting the material.

By injecting the sterilized air or nitrogen to the inside of the resin vessel 1, the material does not enter inside the resin vessel 1, so that it is possible to prevent the coating on the inner surface of the resin vessel 1 and prevent a foreign material from entering the beverage due to the peeling of the coating.

In contrast, the coating or the surface treatment may be performed only on the inner surface of the resin vessel 1. In this case, it is sufficient that the material is prevented from being injected from the outer surface nozzle 21 in the above configuration.

Figure 6:
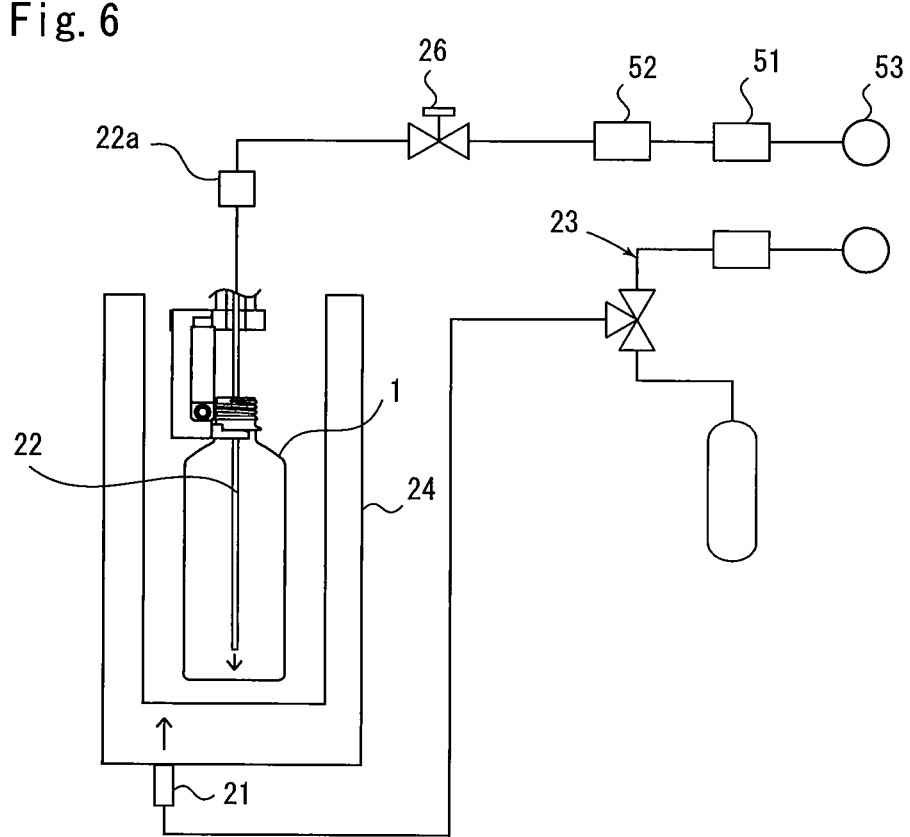
FIG. 6 is a circuit diagram of a coating device according to a second embodiment of the invention.

FIG. 6 is a view showing the surface treatment device 2 for the resin vessel 1 according to a second example, and with respect to the first example, instead of not performing the coating on the inner surface of the resin vessel 1, in order to sterilize the inside of the resin vessel 1, a gas made into a plasma is supplied to the inside of the resin vessel 1 and the irradiation with the electron beam is further performed. Note that the description of the configuration in common with the configuration of the first example will be omitted.

In the present example, similarly to the inner surface nozzle 22 in the first example, the inner surface nozzle 22 for supplying the plasma gas is provided inside the resin vessel 1, and similarly to the inner surface nozzle 22 in the first example, the inner surface nozzle 22 is lifted or lowered by the lifting unit 25.

For supplying the plasma gas to the inner surface nozzle 22, there are provided a plasma generation unit 51 that generates a plasma, a humidity adjustment unit 52 that adjusts the humidity of the plasma gas, and a feeding unit 53 that feeds the plasma gas. The supply of the plasma gas is stopped by the opening/closing valve 26 provided adjacent to the inner surface nozzle 22.

In the present example, the inner surface nozzle 22 supplies the plasma gas on the upstream side of the electron beam irradiation section B similarly to the inner surface injection section A of FIG. 1.

In the inner surface injection section A, the plasma gas is injected to the inside of the resin vessel 1, so that the inside of the resin vessel 1 including the inner surface thereof can be sterilized by the plasma gas.

Subsequently, in the electron beam irradiation section B, the resin vessel 1 is irradiated with the electron beam, so that the outer surface and the inside of the resin vessel 1 can be sterilized by the electron beam. In addition, the plasma gas existing inside the resin vessel 1 is irradiated with the electron beam and is thereby excited to sterilize the inside of the resin vessel 1.

Simultaneously with this, on the outside of the resin vessel 1, the material for the surface treatment, attached to the outer surface of the resin vessel 1 by the irradiation with the electron beam, is activated to perform the coating or the surface modification, and it is thus possible to simultaneously perform the surface treatment on the outer surface and sterilization on the inside.

In each of the above examples, the resin vessel 1 is carried in the state of standing upright and is laterally irradiated with the electron beam, but the resin vessel 1 may be carried in the state of lying down and may be irradiated with the electron beam from above or below.

REFERENCE SIGNS LIST 1 resin vessel
2 surface treatment device
3 sterilization chamber
4 vessel carrier unit
5 material injection unit
6 electron beam irradiation unit
7 aeration unit
21 outer surface nozzle
22 inner surface nozzle
23 supply unit
24 injection booth
25 lifting unit
43 aeration nozzle
51 plasma generation unit

What is claimed is:

1. A surface treatment device for a resin vessel, which performs coating on a surface of the resin vessel, the device comprising:
   a chamber with a pressure set to be equal to or higher than atmospheric pressure;
   a partition plate configured to divide an inside of the chamber into an inner surface injection section and an electron beam irradiation section on a downstream side of the inner surface injection section;

a gripping vessel carrier configured to grip the resin vessel so that the resin vessel is carried and transported from the inner surface injection section to the electron beam irradiation section;

an inner surface nozzle configured to inject a material for coating towards an inner surface of the resin vessel in the inner surface injection section, which resin vessel is carried and transported by the gripping vessel carrier, and attach the material for coating to the inner surface of the resin vessel; and an electron beam irradiator configured to irradiate the resin vessel, which resin vessel is carried and transported by the gripping vessel carrier, with an electron beam in the electron beam irradiation section so as to activate an individual component of the material for coating;

wherein a pressure inside the electron beam irradiation section is set to be higher than a pressure inside the inner surface injection section; and wherein the surface treatment device is configured to attach the material for coating to the inner surface of the resin vessel in the inner surface injection section and thereafter activate the individual component of the material for coating with the electron beam in the electron beam irradiation section so as to form a coating on the inner surface of the resin vessel.

2. The surface treatment device for the resin vessel according to claim 1, wherein the gripping vessel carrier is provided with a gear mechanism configured to rotate the resin vessel by 180 degrees or more in the electron beam irradiation section in which the electron beam irradiator performs the irradiation with the electron beam.

3. The surface treatment device for the resin vessel according to claim 1, wherein the surface treatment device includes a cam mechanism configured to lift or lower the inner surface nozzle, and the inner surface nozzle is caused to enter inside the resin vessel and inject the material for coating.

4. The surface treatment device for the resin vessel according to claim 1, wherein the surface treatment device further comprises a rotation table and a rotation device configured to rotate the resin vessel by 180 degrees or more in the electron beam irradiation section in which the electron beam irradiator performs the irradiation with the electron beam, and the rotation device includes: a rotation element rotatably provided on the rotation table and defining a rotation axis, a pinion gear provided at an upper end of the rotation element, a segment gear swingably provided on the rotation table and meshed with the pinion gear, a cam follower coupled to the segment gear, and a cam provided separately from the rotation table and configured to move the cam follower.

5. The surface treatment device for the resin vessel according to claim 4, wherein the surface treatment device further comprises a lifting device configured to lift or lower the inner surface nozzle in a vertical direction, the lifting device including: a support member that supports the inner surface nozzle, a cam follower provided on the support member, and a cam provided separately from the rotation table; the cam follower of the lifting device following the cam of the lifting device to cause vertical lifting or lowering of the inner surface nozzle, the inner surface nozzle being vertically movable into an interior of the resin vessel by the lifting device to inject the material for coating into the resin vessel towards the inner surface of the resin vessel.

6. The surface treatment device for the resin vessel according to claim 1, wherein the surface treatment device further comprises an injection device disposed in the chamber in the electron beam irradiation section, the injection device including an outer surface nozzle disposed and configured to direct a material towards an outer surface of the resin vessel, and the electron beam irradiator irradiates the material both on the outer surface of the resin vessel and on the inner surface of the resin vessel in the electron beam irradiation section downstream of the inner surface injection section.

* * * * *